United States Patent
Benoist

(10) Patent No.: US 8,219,171 B2
(45) Date of Patent: Jul. 10, 2012

(54) DELIVERY DEVICE FOR IMPLANTABLE MONITOR

(75) Inventor: William Brent Benoist, Germantown, TN (US)

(73) Assignee: Given Imaging Ltd., Yoqneam (IL)

(*) Notice: Subject to any disclaimer, the term of this patent is extended or adjusted under 35 U.S.C. 154(b) by 78 days.

(21) Appl. No.: 12/725,260

(22) Filed: Mar. 16, 2010

(65) Prior Publication Data

US 2011/0230866 A1  Sep. 22, 2011

(51) Int. Cl.
*A61B 5/00* (2006.01)
*A61N 1/00* (2006.01)
*A61K 9/22* (2006.01)

(52) U.S. Cl. .......... 600/343; 600/350; 607/40; 607/116; 607/133; 604/891.1

(58) Field of Classification Search .......... None
See application file for complete search history.

(56) References Cited

U.S. PATENT DOCUMENTS

| | | |
|---|---|---|
| 3,133,537 A | 5/1964 | Muth |
| 3,340,866 A | 9/1967 | Noller |
| 3,480,003 A | 11/1969 | Crites |
| 3,636,956 A | 1/1972 | Schneider |
| 3,739,279 A | 6/1973 | Hollis |
| 3,779,237 A | 12/1973 | Goeltz et al. |
| 3,844,272 A | 10/1974 | Banko |
| 3,949,388 A | 4/1976 | Fuller |
| 4,257,420 A | 3/1981 | Terayama |
| 4,326,535 A | 4/1982 | Steffel et al. |
| 4,503,859 A | 3/1985 | Petty et al. |
| 4,546,436 A | 10/1985 | Schneider et al. |
| 4,561,450 A | 12/1985 | Bryant |
| 4,618,929 A | 10/1986 | Miller et al. |
| 4,638,045 A | 1/1987 | Kohn et al. |
| 4,748,562 A | 5/1988 | Miller et al. |
| 4,823,808 A | 4/1989 | Clegg et al. |
| 4,924,877 A | 5/1990 | Brooks |
| 4,967,759 A | 11/1990 | Teves |
| 4,981,470 A | 1/1991 | Bombeck, IV |
| 4,991,590 A | 2/1991 | Shi |

(Continued)

FOREIGN PATENT DOCUMENTS

JP  05-023322  2/1993

(Continued)

OTHER PUBLICATIONS

Anggiansah et al., "Primary Peristalsis is the Major Acid Clearance Mechanism in Reflux Patients," Gut 35: pp. 1536-1542, 1994.

(Continued)

*Primary Examiner* — Betty Forman

(74) *Attorney, Agent, or Firm* — Pearl Cohen Zedek Latzer, LLP

(57) ABSTRACT

A system, device, and method for placing a capsule for sensing one or more parameters of a patient by anchoring the capsule to a tissue at a specific site and releasing the capsule from the device, using a single actuator operated during a single motion. As an example, a delivery device may anchor the capsule to the tissue site and release the capsule from the delivery device during a single motion of the actuator. This allows a user to place the capsule by interacting with only a single actuator through one type of motion, thus making delivery of the capsule more reliable and user-friendly.

19 Claims, 11 Drawing Sheets

U.S. PATENT DOCUMENTS

| | | | |
|---|---|---|---|
| 5,018,529 A | 5/1991 | Tenerz et al. |
| 5,063,081 A | 11/1991 | Cozzette et al. |
| 5,080,663 A | 1/1992 | Mills |
| 5,108,889 A | 4/1992 | Smith |
| 5,117,827 A | 6/1992 | Stuebe et al. |
| 5,127,404 A | 7/1992 | Wyborny et al. |
| 5,153,584 A | 10/1992 | Engira |
| 5,247,938 A | 9/1993 | Silverstein et al. |
| 5,269,789 A | 12/1993 | Chin et al. |
| 5,297,437 A | 3/1994 | Schneider |
| 5,301,673 A | 4/1994 | Rabito et al. |
| 5,368,027 A | 11/1994 | Lubbers et al. |
| 5,381,800 A | 1/1995 | Angelchik |
| 5,394,882 A | 3/1995 | Mawhinney |
| 5,398,844 A | 3/1995 | Zaslavsky et al. |
| 5,479,935 A | 1/1996 | Essen-Moller |
| 5,486,818 A | 1/1996 | Loponen |
| 5,497,772 A | 3/1996 | Schulman et al. |
| 5,624,453 A | 4/1997 | Ahmed |
| 5,697,384 A | 12/1997 | Miyawaki |
| 5,720,771 A | 2/1998 | Snell |
| 5,759,199 A | 6/1998 | Snell et al. |
| 5,792,153 A | 8/1998 | Swain et al. |
| 5,833,625 A | 11/1998 | Essen-Moller |
| 5,836,895 A | 11/1998 | Ramsey, III |
| 5,843,139 A | 12/1998 | Goedeke et al. |
| 5,862,803 A | 1/1999 | Besson et al. |
| 5,873,369 A | 2/1999 | Laniado et al. |
| 5,899,931 A | 5/1999 | Deschamp et al. |
| 5,935,078 A | 8/1999 | Feierbach |
| 5,938,585 A | 8/1999 | Donofrio |
| 5,957,854 A | 9/1999 | Besson et al. |
| 5,967,986 A | 10/1999 | Cimochowski et al. |
| 5,984,875 A | 11/1999 | Brune |
| 6,021,352 A | 2/2000 | Christopherson et al. |
| 6,088,608 A | 7/2000 | Schulman et al. |
| 6,190,353 B1 | 2/2001 | Makower et al. |
| 6,285,897 B1 | 9/2001 | Kilcoyne et al. |
| 6,285,899 B1 | 9/2001 | Ghaem et al. |
| 6,304,766 B1 | 10/2001 | Colvin, Jr. |
| 6,358,197 B1 | 3/2002 | Silverman et al. |
| 6,398,710 B1 | 6/2002 | Ishikawa et al. |
| 6,402,689 B1 | 6/2002 | Scarantino et al. |
| 6,406,498 B1 | 6/2002 | Tormala et al. |
| 6,409,674 B1 | 6/2002 | Brockway et al. |
| 6,416,471 B1 | 7/2002 | Kumar et al. |
| 6,535,764 B2 | 3/2003 | Imran et al. |
| 6,585,644 B2 | 7/2003 | Lebel et al. |
| 6,689,056 B1 | 2/2004 | Kilcoyne et al. |
| 6,699,186 B1 | 3/2004 | Wolinsky |
| 6,994,712 B1 | 2/2006 | Fisher et al. |
| 7,020,531 B1 | 3/2006 | Colliou et al. |
| 7,052,474 B2 | 5/2006 | Castell et al. |
| 7,066,879 B2 | 6/2006 | Fowler et al. |
| 7,175,660 B2 | 2/2007 | Cartledge et al. |
| 7,189,247 B1 | 3/2007 | Zirps et al. |
| 7,371,215 B2 | 5/2008 | Colliou et al. |
| 7,448,993 B2 | 11/2008 | Yokoi et al. |
| 7,479,108 B2 | 1/2009 | Rini et al. |
| 7,621,036 B2 | 11/2009 | Cros et al. |
| 7,654,985 B2 | 2/2010 | Dinsmoor et al. |
| 7,695,512 B2 | 4/2010 | Lashinski et al. |
| 2002/0042562 A1 | 4/2002 | Meron et al. |
| 2002/0103424 A1* | 8/2002 | Swoyer et al. ............... 600/350 |
| 2003/0092964 A1 | 5/2003 | Kim |
| 2003/0216622 A1 | 11/2003 | Meron et al. |
| 2004/0133089 A1 | 7/2004 | Kilcoyne et al. |
| 2004/0158125 A1 | 8/2004 | Aznoian et al. |
| 2004/0158138 A1 | 8/2004 | Kilcoyne et al. |
| 2004/0260164 A1 | 12/2004 | Kilcoyne et al. |
| 2004/0260346 A1 | 12/2004 | Overall et al. |
| 2005/0143624 A1 | 6/2005 | Iddan |
| 2005/0165419 A1 | 7/2005 | Sauer et al. |
| 2005/0209653 A1 | 9/2005 | Herbert et al. |
| 2005/0245840 A1 | 11/2005 | Christopherson et al. |
| 2005/0288555 A1 | 12/2005 | Binmoeller |
| 2006/0247724 A1 | 11/2006 | Gerber et al. |
| 2007/0270651 A1 | 11/2007 | Gilad et al. |
| 2008/0091177 A1 | 4/2008 | Christian |
| 2008/0228193 A1* | 9/2008 | Matityahu ...................... 606/99 |
| 2010/0131016 A1 | 5/2010 | Gerber et al. |
| 2010/0137686 A1 | 6/2010 | Meron et al. |
| 2010/0217368 A1 | 8/2010 | Dinsmoor et al. |

FOREIGN PATENT DOCUMENTS

| | | |
|---|---|---|
| JP | 06-142081 | 5/1994 |
| WO | WO 98/02209 | 1/1998 |
| WO | WO 01/12102 | 2/2001 |
| WO | WO 02/087657 | 11/2002 |
| WO | WO 2006/099425 | 9/2006 |

OTHER PUBLICATIONS

Johnsson et al., "Determinants of Gastroesophageal Reflux and their Inter-relationships," Br. J. Surg, vol. 76, No. 3, pp. 241-244, Mar. 1989.

Bravo pH Monitoring System Brochure, Given Imaging, Jun. 2010.

Kadirkamanathan S.S. et al., "An ambulant porcine model of acid reflux used to evaluate endoscopic gastroplasty," Gastrointestinal Science Research Unit, The London Hospital, pp. 782-788, 1999.

"Implantable Biotelemetry System for Preterm Labor and Fetal Monitoring," National Aeronautics and Space Administration, Ames Research Center. printed Nov. 7, 2011.

Swain, C.P. et al., "An endoscopically deliverable tissue-transfixing device for securing biosensors in the gastrointestinal tract," Gastrointestinal Endoscopy, vol. 40, No. 6, 1994.

Hines et al., "pH Biotelemetry Transmitter", Improving Space Travel, Human Exploration and Development of Space Enterprise, pp. 148-149.

Bluck, J., "Miniaturized Transmitter to be Used in Efforts to Save Babies," NASA Ames Research Center, Nov. 18, 1998 e-mail, Release 98-65AR.

* cited by examiner

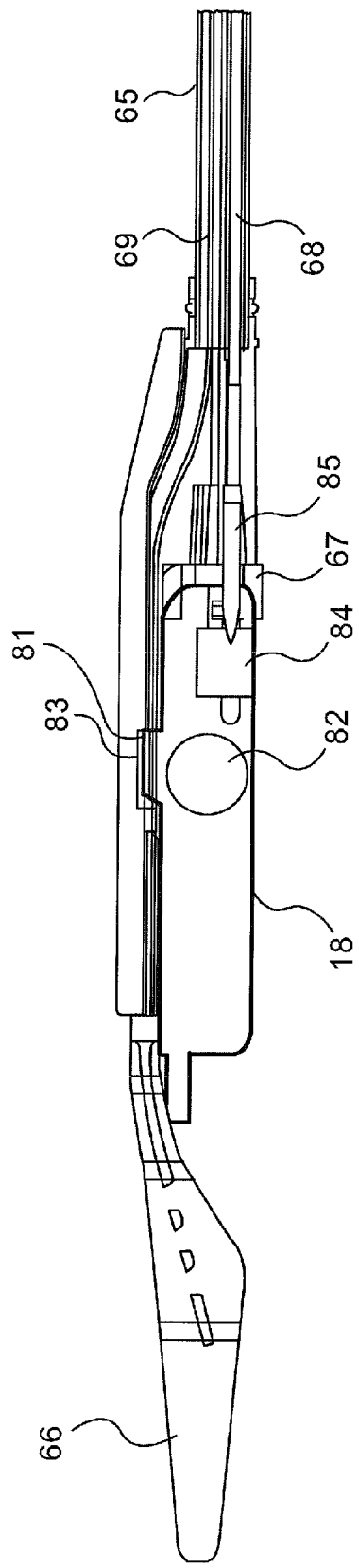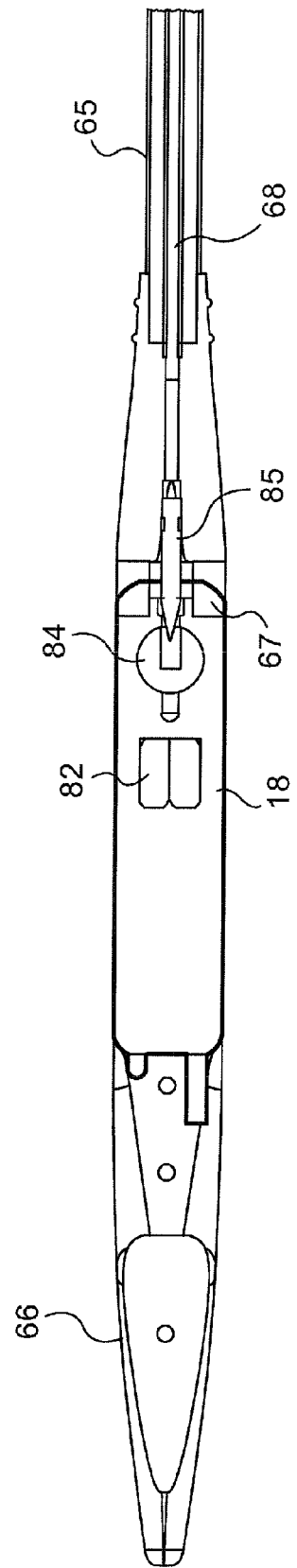
FIG. 7A
FIG. 7B

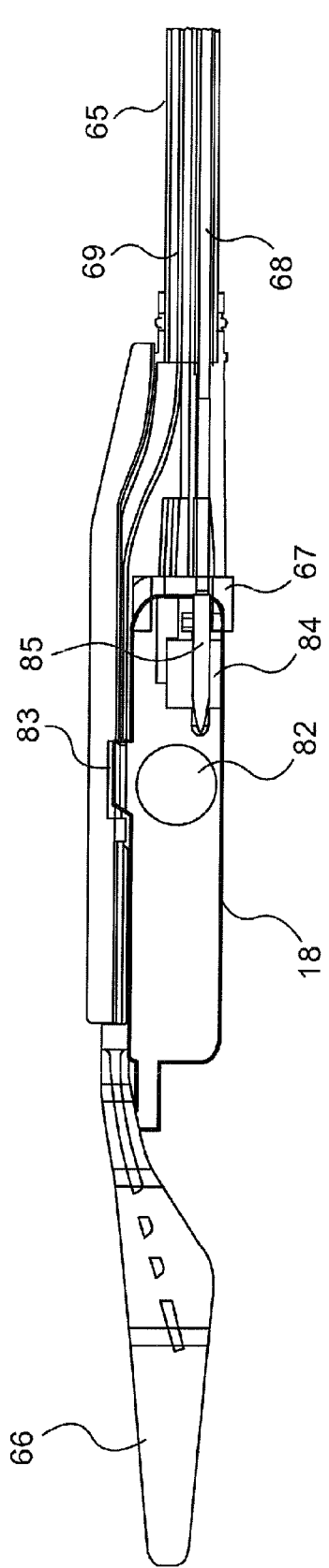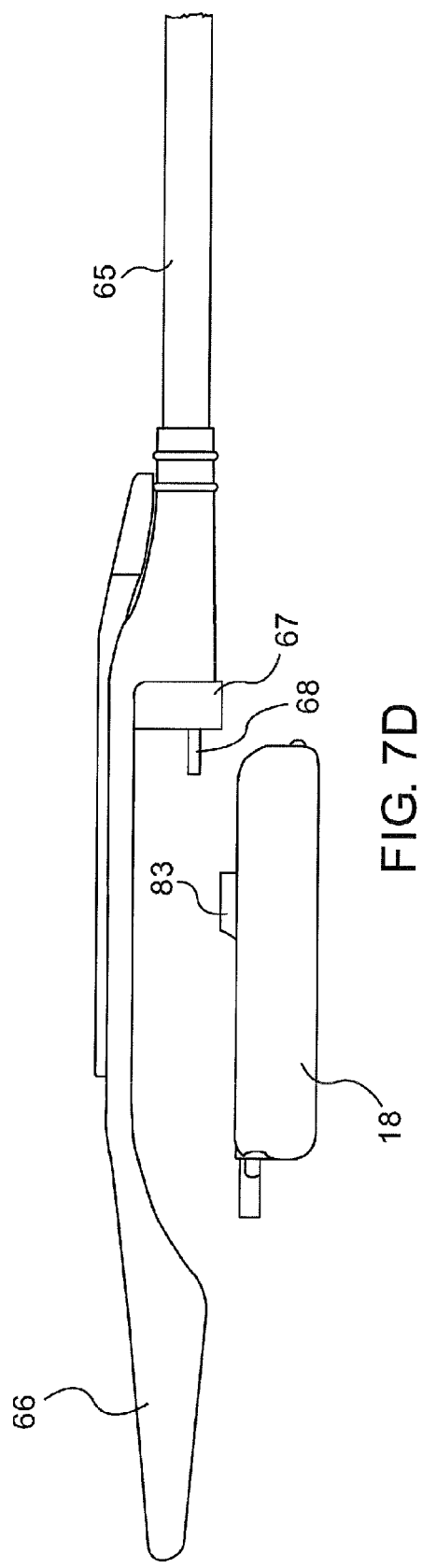

DELIVERY DEVICE FOR IMPLANTABLE MONITOR

TECHNICAL FIELD

This disclosure relates to medical devices and, more particularly, to medical devices for monitoring physiological conditions within a body lumen.

BACKGROUND OF THE INVENTION

Modern medicine uses a variety of monitoring systems and methods, some of which require attachment of a small capsule to a tissue or organ inside the body. One such use is in monitoring Gastroesophageal reflux for diagnosing gastroesophageal reflux disease. Gastroesophageal reflux occurs when stomach acid intermittently surges into the esophagus. It is common for most people to experience this acid reflux occasionally as heartburn. Gastroesophageal reflux disease (GERD) is a clinical condition in which the reflux of stomach acid into the esophagus is frequent enough and severe enough to impact a patient's normal functioning and/or to cause damage to the esophagus.

In the lower part of the esophagus, where the esophagus meets the stomach, there is a muscular valve called the lower esophageal sphincter (LES). Normally, the LES relaxes to allow food to enter into the stomach from the esophagus. The LES then contracts to prevent stomach acids from entering the esophagus. In patients afflicted with GERD, the LES relaxes too frequently or at inappropriate times, allowing stomach acids to reflux into the esophagus.

The most common symptom of GERD is heartburn. Acid reflux also leads to esophageal inflammation, which causes symptoms such as painful swallowing and difficulty swallowing. Pulmonary symptoms such as coughing, wheezing, asthma, or inflammation of the vocal cords or throat may occur in some patients. More serious complications from GERD include esophageal ulcers and narrowing of the esophagus. The most serious complication from chronic GERD is a condition called Barrett's esophagus in which the epithelium of the esophagus is replaced with abnormal tissue. Barrett's esophagus is a risk factor for the development of cancer of the esophagus.

Accurate diagnosis of GERD is difficult but important. Accurate diagnosis allows identification of individuals at high risk for developing the complications associated with GERD. It is also important to be able to differentiate between gastroesophageal reflux, other gastrointestinal conditions, and various cardiac conditions. For example, the similarity between the symptoms of a heart attack and heartburn often lead to confusion about the cause of the symptoms. Esophageal manometry, esophageal endoscopy, and esophageal pH monitoring are standard methods of measuring esophageal exposure to stomach acids and are currently used to diagnose GERD.

One example for an esophageal pH monitoring device is the Bravo™-brand pH monitoring system, available from Given Imaging Ltd. of Yoqneam, Israel. In the currently available Bravo™ pH monitoring system, an autonomous pH monitoring capsule is attached to the esophagus in order to monitor esophageal pH. A delivery device that anchors the capsule to the esophagus has a single actuator. However, when operating the Bravo™ delivery device, two different motions are required from the operator; a first motion of the actuator anchors the capsule at a specific location along the esophagus, and a second motion of the actuator releases the capsule from the delivery device. Although operating the single actuator is not complicated, it is not intuitive for some users, and requires some training for proper use. Therefore, there is a need for a simpler delivery device for anchoring a monitoring capsule within the body lumen.

SUMMARY OF THE DISCLOSURE

In general, this disclosure describes devices and methods for affixing or anchoring a capsule for sensing one or more parameters within a body lumen of a patient. According to embodiments of the invention, a delivery device may be configured to anchor the capsule to tissue at a specific site within the body lumen and release the capsule from the delivery device during a single motion of an actuator. In this manner, a user may place the capsule by interacting with a single actuator in only one motion. Such an arrangement according to embodiments of the invention may be easy to operate and allow stability of the delivery device during operation. Furthermore, delivery devices according to embodiments of the invention may be less expensive to manufacture and easier to assemble than prior art delivery devices, since they contain one actuator that operates in one type of motion, rather than operating using two types of motion.

In one embodiment of the invention, a device may comprise an elongated probe configured to carry at a distal end thereof an implantable capsule for deployment within a patient, an anchor element configured to anchor the capsule to tissue within the patient, a release mechanism configured to release the capsule from the probe, and an actuator configured to activate the anchor element to cause the anchor element to anchor the capsule to the tissue, and activate the release mechanism to release the capsule from the probe by a single motion of the actuator.

In some embodiments of the invention, the single motion of the actuator may comprise a pulling motion, while the actuator may be a movable trigger turning around a pivot.

In some embodiments of the invention, the device may comprise a vacuum inlet that is adapted to be coupled to a vacuum source. In some embodiments of the invention, the device may be configured to provide suction to draw the tissue into a void of the capsule. In some embodiments of the invention, the device may comprise a vacuum seal. The actuator may be configured to push the vacuum seal over the vacuum inlet during the single motion of the actuator such that suction may be ceased.

According to some embodiments of the invention, the device may comprise a capsule coupling mechanism configured to couple the capsule to a distal end of the probe, wherein the release mechanism may cause the capsule coupling mechanism to release the capsule during the single motion of the actuator. The capsule coupling mechanism may include at least one pull-wire configured to couple to the capsule. In some embodiments of the invention, the release mechanism may cause the pull-wire to retract and thereby to release the capsule during the single motion of the actuator.

According to some embodiments of the invention, the device may further comprise a locking pin, wherein the actuator may engage with the locking pin to advance the locking pin through the tissue during the single motion. In some embodiments of the invention, the device may comprise a push-wire, wherein the actuator may engage with the push-wire to advance the locking pin through the tissue during the single motion of the actuator.

According to some embodiments of the invention, the device may comprise a locking mechanism that prevents the trigger to move before pulled by the operator.

In an embodiment of the invention, a method of operation may comprise delivering an implantable capsule to tissue within a patient using a delivery device, anchoring the implantable capsule to the tissue, and releasing the capsule from the delivery device during a single motion of an actuator of the delivery device.

According to some embodiments of the invention, anchoring the capsule to the tissue may comprise advancing a locking pin through the tissue during the single motion of the actuator.

In some embodiments of the invention, the method may further comprise coupling the capsule to a distal end of the device using at least one pull-wire, wherein releasing the capsule from the device may comprise retracting the pull-wire to release the capsule.

In some embodiments of the invention, the capsule may include a sensor and thus the method may further comprise: measuring one or more parameters of the patient via the sensor of the capsule; and transmitting the measured parameters from the capsule to a receiver.

In some embodiments of the invention, the tissue to which the capsule is anchored may be the esophagus. The method may further comprise providing suction to the tissue to draw a portion of the tissue into a void of the capsule, wherein anchoring the capsule to the tissue comprises anchoring the capsule to the portion of the tissue drawn into the void of the capsule. In some embodiments of the invention, the step of releasing the capsule from the delivery device may comprise stopping suction to the tissue.

In a further embodiment of the invention, a device may comprise means for carrying an implantable capsule for deployment within a patient, means for anchoring the capsule to tissue within the patient, means for releasing the capsule from the carrying means, and means for activating the anchoring means to anchor the capsule to the tissue and activating the releasing means to release the capsule from the carrying means during a single motion of the activating means. In some embodiments of the invention, the device may further comprise means for coupling the capsule to the carrying means, wherein the releasing means may cause the coupling means to release the capsule during the single motion of the activating means.

In another embodiment of the invention, a system may comprise a delivery apparatus including an elongated probe configured to carry at a distal end thereof an implantable capsule for deployment within a patient, a release mechanism configured to release the capsule from the probe, and an actuator to control delivery of the capsule. A system according to embodiments of the invention may further include an anchor element configured to anchor the capsule to tissue within the patient. The actuator may be configured to activate the anchor element to cause the anchor element to anchor the capsule to the tissue, and to activate the release mechanism to release the capsule from the probe by a single motion of the actuator.

The details of one or more embodiments are set forth in the accompanying drawings and the description below. Other features, objects, and advantages of the described techniques will be apparent from the description and drawings, and from the claims.

BRIEF DESCRIPTION OF THE DRAWINGS

FIGS. 7A, 7B, 7C, and 7D are schematic diagrams illustrating exemplary operation of a distal end of the delivery device according to an embodiment of the invention during various stages of delivery of a capsule.

Figure 1:
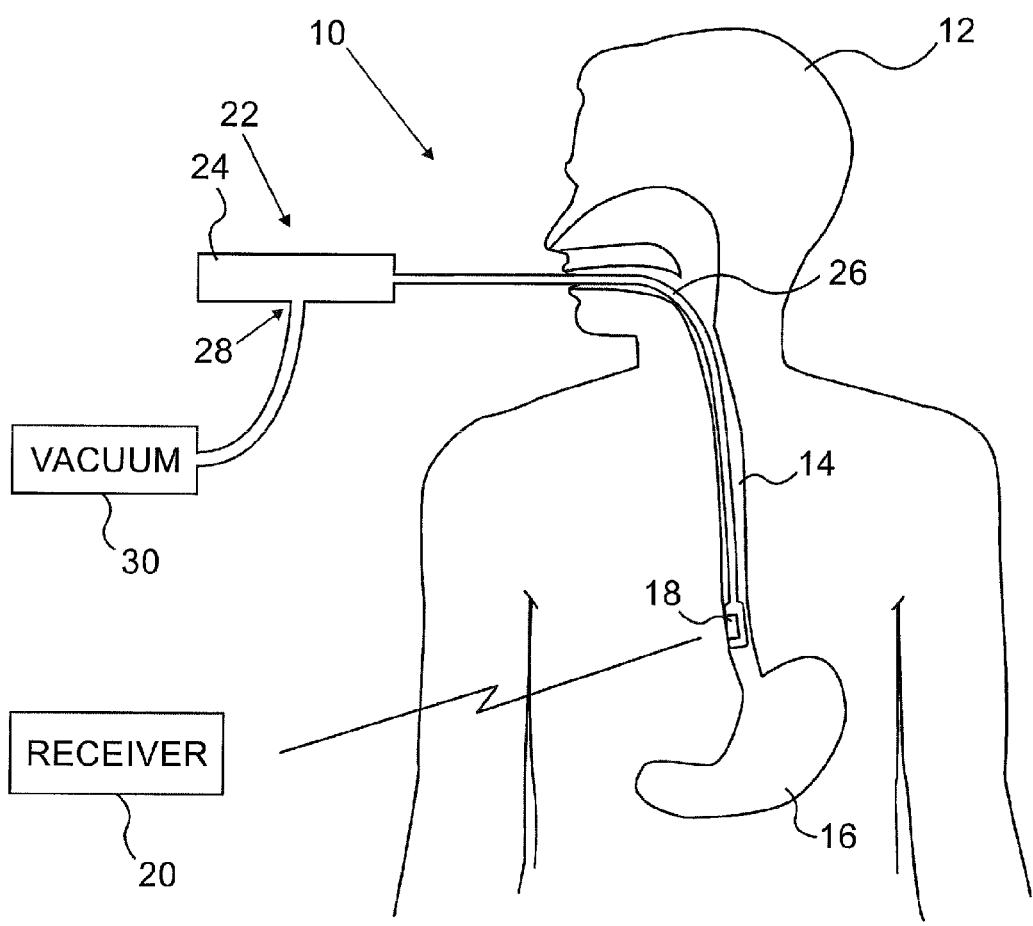
FIG. 1 is a schematic diagram illustrating an esophageal acidity monitoring system according to embodiments of the present invention shown in conjunction with a patient.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Although the below description refers to a pH monitoring capsule, it will be understood that embodiments of the present invention may be used in connection with attaching any sensing or monitoring device to a body lumen. A delivery device may be configured to anchor the capsule to tissue at a specific site within the body lumen, and release the capsule from the delivery device during a single motion of the actuator, e.g., linear or arcuate motion of the actuator in a single direction or with a single movement. In this manner, a user may attach the capsule and disengage the capsule from the delivery device by interacting with a single actuator, operating it in only one easy, continuous motion.

FIG. 1 is a schematic diagram illustrating an acidity monitoring system 10 shown in conjunction with a patient 12. Acidity monitoring system 10 measures the acidity within the lower portion of an esophagus 14 of patient 12. More specifically, acidity monitoring system 10 measures the acidity level near the lower esophageal sphincter (LES) of patient 12, i.e., where esophagus 14 meets stomach 16. Measuring the acidity level of the lower portion of esophagus 14 allows a physician to diagnose Gastroesophageal Reflux Disease (GERD). Although system 10 is described in this disclosure in terms of sensing acidity in the esophagus, the system may be adapted for application to a variety of other sensing environments, and to a variety of different sensing applications. In other words, system 10 may be used for monitoring other locations within patient 12 or monitoring other body parameters.

As described above, the LES normally relaxes to allow food to enter into stomach 16 from esophagus 14. The LES then contracts to prevent stomach contents from entering esophagus 14. In a patient with GERD, the LES relaxes too frequently or at inappropriate times allowing stomach contents to reflux into the esophagus 14, increasing the acidity level near the lower portion of esophagus 14, which may lead to complications such as heartburn, painful swallowing, difficulty swallowing, coughing, wheezing, asthma, inflammation of the vocal cords or throat, esophageal ulcers, narrowing of the esophagus, and in the worst cases Barrett's esophagus.

Acidity monitoring system 10 includes a capsule 18 for sensing acidity. Capsule 18 includes an acidity sensor, e.g., a pH sensor (not shown), to measure the acidity level within esophagus 14. The pH sensor carried by capsule 18 may generally conform to the pH sensor employed in monitoring devices, such as those described in U.S. Pat. Nos. 6,285,897 and 6,689,056 to Kilcoyne, et al., the entire contents of which are incorporated herein by reference. Capsule 18 may include a transmitter and an antenna (not shown) for wireless communication with receiver 20, whereby capsule 18 may transmit measured acidity data to receiver 20. Receiver 20 may, for example, comprise a portable receiver to be carried by patient 12. Receiver 20 may store the data wirelessly transmitted by capsule 18. The information stored within receiver 20 may be downloaded by a physician to a computing device (not shown) and analyzed to diagnose the condition of patient 12. Alternatively, capsule 18 may include a memory that stores the measured data, thus permitting recovery of the data after capsule 18 is passed through patient 12.

A delivery device 22 may be used to attach capsule 18 to a wall of esophagus 14 and, more particularly, to esophageal tissue within esophagus 14. Delivery device 22 includes a proximal portion, referred to herein as a handle 24, and an elongated probe 26 that extends from handle 24 and ends in a distal portion. In use, the distal portion is inserted into esophagus 14 of patient 12. Elongated probe 26 is configured to carry at a distal end thereof capsule 18 for deployment within patient 12. Capsule 18 may, for example, be coupled to a distal end of delivery device 22 for delivery to a particular location within esophagus 14. As will be described in detail below, delivery device 22 may utilize an actuator, such as a movable trigger (not shown), to both anchor capsule 18 to esophagus 14 and release the capsule from delivery device 22 during a single motion.

In the example of FIG. 1, delivery device 22 includes a vacuum inlet 28 on handle 24 to couple delivery device 22 to a vacuum source 30. Vacuum source 30 applies suction within an inner lumen formed by probe 26. A vacuum outlet (not shown), located in a void within capsule 18, applies the suction from vacuum source 30 to the wall of esophagus 14 in order to draw esophageal tissue into a void within capsule 18. For example, the vacuum level required for drawing tissue into the void within capsule 18 may be around 508-635 mm Hg. Delivery device 22 anchors capsule 18 to the esophageal tissue drawn into the void of capsule 18 and disengages from capsule 18, thereby leaving capsule 18 attached to the wall of esophagus 14.

According to some embodiments, there may be an additional action performed by the single actuator in addition to anchoring the capsule 18 to the wall of esophagus 14 and disengaging the delivery device 22 from capsule 18. The single trigger may additionally close vacuum inlet 28 so that suction may no longer be applied through delivery device 22. As long as vacuum is applied through delivery device 22, a suction force might keep capsule 18 attached to delivery device 22. In order for capsule 18 to easily disengage from delivery device 22, there is a need to stop the vacuum, since the vacuum increases the force that attaches the capsule to the delivery device. Therefore, the single trigger may close the vacuum inlet 28 after it anchors capsule 18 to the wall of esophagus 14 and before it disengages capsule 18 from delivery device 22.

In particular, the actuator is configured to activate an anchor element to anchor capsule 18 to the wall of esophagus 14. The actuator is also configured to activate a release mechanism to cause a retention mechanism coupled to capsule 18 to detach from capsule 18, thus releasing capsule 18 from delivery device 22. According to embodiments of the invention, the actuator may anchor the capsule 18 to the wall of esophagus 14, close the vacuum inlet 28, thereby ceasing suction between the capsule 18 and delivery device 22, and release capsule 18 from the delivery device 22. According to some embodiments of the invention, all three actions may be performed in sequence by a single motion. The single motion may be a "trigger pulling" motion. Allowing the physician to place capsule 18 with a single actuator activated in one continuous motion, in accordance with embodiments of the present invention, may make the delivery system more reliable and more user-friendly.

While on the wall of esophagus 14, the acidity sensor of capsule 18 obtains acidity measurements for a period of time, e.g., several hours or several days, and relays the acidity measurements to receiver 20 via wireless communication. Capsule 18 eventually detaches from the wall of the esophagus 14 and is passed through the digestive system of patient 12. It will be recognized that for some applications, capsule 18 may be designed for more persistent placement in the esophagus or in other body lumens, tissue sites, or organs, such that the capsule may remain attached within the patient for several weeks, months, or possibly years.

Although the present description refers to delivering a capsule 18 for sensing acidity of esophagus 14 of the patient, it will be recognized that embodiments of the invention are applicable to delivery of any other applicable type of sensor to any suitable tissue location or organ. Moreover, the inventions of the present disclosure may be used to place other therapeutic devices, drugs or other agents to locations within patient 12.

Figure 2:
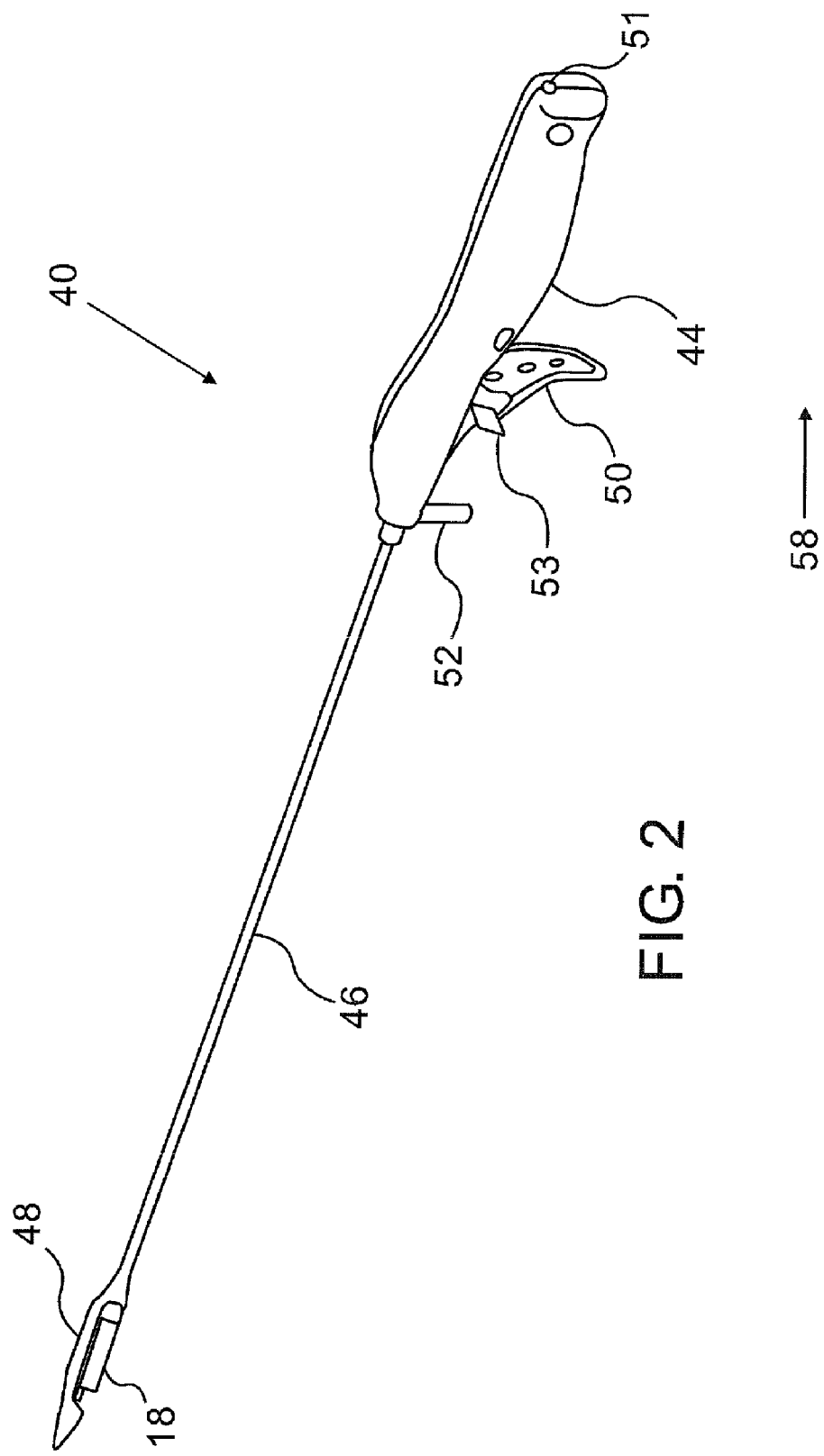
FIG. 2 is a perspective diagram illustrating an exemplary delivery device according to an embodiment of the invention for placing a capsule at a location within body lumen of a patient.

Reference is made to FIG. 2, which is a schematic diagram illustrating an exemplary delivery device 40 for delivering a capsule 18 to a location within a patient, for example, as shown in FIG. 1. Delivery device 40 may include a handle 44 and an elongated probe 46 extending from handle 44. Delivery device 40 may also include a capsule coupling mechanism 48 at a distal end of probe 46 that may be detachably coupled to capsule 18 to secure capsule 18 to delivery device 40 during placement of capsule 18. As described below, delivery device 40 may place capsule 18 at an appropriate tissue location along esophagus 14 (FIG. 1), anchor capsule 18 to the appropriate location, close vacuum inlet 52 so as to stop tissue suction, and release capsule 18, substantially all during a single motion of the actuator 50. In this manner, delivery device 40 is capable of anchoring capsule 18 to a tissue location and releasing capsule 18 from delivery device 40 using a single actuator 50.

According to some embodiments of the invention, delivery device 40 may comprise an actuator, or trigger 50 that may be easily pulled and may thus activate anchoring and releasing of capsule 18 from delivery device 40. Actuator 50 may be located at the proximal end of the elongated delivery device 40. According to some embodiments, one pull of trigger 50 may cause at least three actions to take place. First, capsule 18 may be anchored to the tissue wall of esophagus 14 (FIG. 1). Then, vacuum inlet 52 may be closed such that suction is ceased and capsule 18 is no longer attached to delivery device 40 by suction (only by other mechanical means). Finally, capsule 18 may be released from the delivery device 40, leaving capsule 18 to remain attached to the wall of esophagus 14. In some embodiments of the invention, actuator 50 may be manually activated, e.g., by a physician's hand, or automatically activated, e.g., by a motor or other drive mechanism in response to physician action. Delivery device 40 may include a locking mechanism 53 and pull-tab 51, described further below.

The distal end of delivery device 40, which carries capsule 18, may be inserted into esophagus 14 and extended through esophagus 14 to a location five to six centimeters above the LES, i.e., the tissue location of interest in this example. The distal end of delivery device 40 may be guided to the LES using any of a number of different techniques. For example, delivery device 40 may detect a pressure variation, such as a pressure variation between the stomach and the esophagus, to identify the location of the LES. Alternatively, the user of delivery device 40 may use external imaging techniques, such as endoscopy, ultrasound, or fluoroscopy, to track the location of the distal end of delivery device 40. In another embodiment, the distal end of delivery device 40 may be inserted into esophagus of patient 12 until a depth marker (not shown), which may be located along probe 46, reaches a particular location. The depth marker may be moved up or down probe 46 based on the approximate length of esophagus 14 of patient 12.

Upon identifying the appropriate location for placement of capsule 18, delivery device 40 may be connected to vacuum source 30 and suction may be applied through vacuum inlet 52. Actuator 50 may control closing of vacuum inlet 52 and, thus, application (or cessation) of suction from vacuum source 30 (FIG. 1). Actuator 50 may allow application of suction through vacuum inlet 52 prior to actuation of actuator 50. That is, by default, once vacuum source 30 is attached to vacuum inlet 52 and turned on, vacuum inlet 52 may receive sufficient suction pressure from vacuum source 30 to draw a portion of esophageal tissue into a void 84 (shown in FIGS. 7A-7C) of capsule 18. Sufficient suction pressure from vacuum source 30 may provide contact between capsule 18 and the esophageal tissue, and may further secure capsule 18 within delivery device 40. When actuator 50 is activated, one of the actions occurring during activation of actuator 50 may be closure of vacuum inlet 52. When vacuum inlet 52 is closed suction may cease, and capsule 18 may be easily released from delivery device 40 during activation of actuator 50.

Upon drawing the esophageal tissue into void 84 (FIGS. 7A-7C), actuator 50 may be adjusted to cause delivery device 40 to anchor capsule 18 to the esophageal tissue drawn into void 84. In one embodiment, actuator 50 may be pulled toward the proximal end of delivery device 40, in the direction of arrow 58, to cause the push wire 68 (FIG. 3) to deploy an anchor element configured to anchor sensing capsule 18 to a wall of esophagus 14. For example, the push wire 68 may deploy a pin 85 (FIGS. 7A-7C) through the esophageal tissue when actuator 50 is pulled and turns around its pivot 54 (FIG. 3).

After capsule 18 is anchored to the wall of esophagus 14, and vacuum inlet 52 is closed, delivery device 40 may release capsule 18, thereby leaving capsule 18 attached to the wall of esophagus 14. Delivery device 40 may release capsule 18 during the same pivot motion of the actuator 50. In particular, when actuator 50 continues to be pulled, thus causing it to rotate around pivot 54 (FIG. 3), the actuator 50 may activate a release mechanism that releases capsule 18 from delivery device 40. As an example, the pivot motion of the actuator 50 may cause a pull wire 69 that is passed through capsule 18 and holds it within delivery device 40 (as shown in FIGS. 7A-7C), to retract toward the proximal end of delivery device 40, thus releasing capsule 18 from delivery device 40. In this manner, delivery device 40 may anchor capsule 18 to the tissue and release capsule 18 from delivery device 40 using a single actuator operated in only one continuous motion.

Delivery device 40 may then be removed and a sensor of capsule 18 may begin to measure one or more parameters of esophagus 14 over time and transmit the information to receiver 20 via wireless communication, e.g., via a transmitter and an antenna. As an example, the sensor of capsule 18 may measure one or more parameters that indicate an acidity of esophagus 14. Such operation is described above with respect to FIG. 1.

Figure 3:
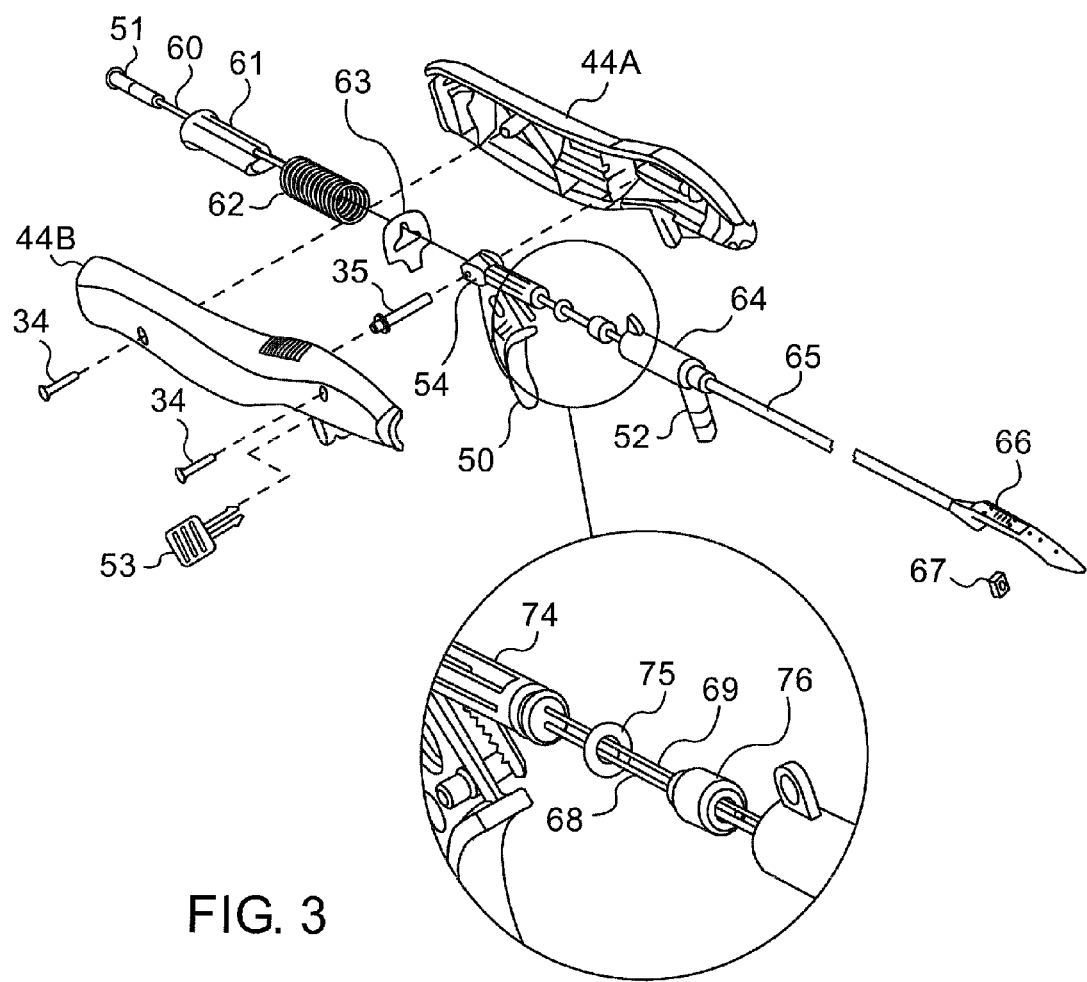
FIG. 3 is a schematic diagram illustrating an exploded view of the delivery device according to an embodiment of the invention shown in FIG. 2.

Reference is made to FIG. 3 which is a schematic diagram illustrating an exploded view of exemplary delivery device 40 of FIG. 2. The exploded view of delivery device 40 illustrates various example components of delivery device 40. Delivery device 40 may include a locking mechanism 53. Locking mechanism or safety lock 53 may lock actuator 50 to prevent inadvertent movement of actuator 50 during packing, shipping or unpacking, or when vacuum is first applied, which could cause trigger 50 to move by suction force instead of by user initiation. When safety lock 53 is coupled to actuator 50, actuator 50 is unable to move in any direction. According to some embodiments of the invention, safety lock 53 prevents actuator 50 from being spontaneously pulled without a user initiating the activation of actuator 50. Safety lock 53 is disengaged prior to use of delivery device 40, and only then is actuator 50 free to be pulled by a user operating delivery device 40.

Delivery device 40 may include a left handle body 44A and right handle body 44B. Left handle body 44A and right handle body 44B may couple together to form the body of handle 44 (FIG. 2). The left handle body 44A and the right handle body 44B may be attached through pins 34. In other embodiments, the left handle body 44A and right handle body 44B may be attached through other means such as welding, adhesive, etc. Actuator 50 may fit in between left handle body 44A and right handle body 44B and may be activated in response to force applied by a user of the device. Actuator 50 may be secured by pin 35 to pivot 54, around which it rotates when pulled by a user.

The lower part of both left handle body 44A and right handle body 44B may be formed to include a vacuum inlet 52 that couples to a vacuum source 30 (FIG. 1) to provide suction. Vacuum inlet 52 may be part of T-tube 64 connected to the capsule cradle 66 through tube 65. Two wires may pass through tube 65: push wire 68 and pull wire 69. Push wire 68 may push the anchor element (e.g., a pin) into the esophageal tissue sucked into void 84 (FIG. 7A). Pull wire 69 may pass through an opening in protrusion 81 (FIG. 7A) of capsule 18, located parallel to the capsule's longitudinal axis, and through a correlating opening in dent 83 of delivery device 40 located at the capsule cradle 66, parallel to the opening in protrusion 81. When pull-wire 69 is retracted towards the proximal end of delivery device 40, e.g., when it is pulled back by activation of trigger 50, pull-wire 69 does no longer pass through the opening in protrusion 81 and capsule 18 may be released from delivery device 40.

In some embodiments, the capsule cradle 66 may include a seal 67, which may be positioned between the capsule 18 and the proximal end of capsule cradle 66. Seal 67 may ensure that capsule 18 is tightly attached to capsule cradle 66 and thus ensure vacuum is delivered into capsule 18 without any leaks.

Trigger 50 may be attached to T-tube stem 74, which may be inserted into T-tube 64 during assembly of delivery device 40. Pull-wire 69 may pass through T-tube stem 74 and into T-tube 64 until it reaches the capsule cradle 66. Push-wire 68 may be connected to T-tube stem 74 and may pass through T-tube 64 until it reaches the capsule cradle 66. Push-wire 68 and pull-wire 69 may further be threaded through T-tube vacuum seal 76, which may be located between T-tube stem 74 and T-tube 64. In some embodiments, an intermediator 75, e.g. an O-ring, may be positioned between T-tube stem 74 and T-tube vacuum seal 76 in order to create a seal at the interface between T-tube stem 74 and T-tube vacuum seal 76. Intermediator 75 may be of a shape other than an O-ring. Intermediator 75 may be made of various materials; however, intermediator 75 is typically made of materials with high elasticity. T-tube vacuum seal 76 may close vacuum inlet 52 once trigger 50 is pulled. Once actuator/trigger 50 is pulled by a user of delivery device 40, T-tube stem 74 is pushed forward toward the distal end of delivery device 40, thus pushing T-tube vacuum seal 76 forward, toward the distal end of delivery device. Specifically, T-tube vacuum seal 76 may be pushed to cover the opening in vacuum inlet 52 through which vacuum is applied to delivery device 40, after the capsule 18 is anchored to the esophageal tissue.

As will be described in detail, when trigger 50 is pulled three actions may occur in sequence. During the first action, the capsule may be anchored to the esophageal tissue. During the second action, and while the trigger 50 is further pulled back (during the same continuous pull), the vacuum inlet 52 may be covered and sealed by T-tube vacuum seal 76. During the third action, while trigger 50 is pulled all the way toward the proximal end of delivery device 40 (completing the same continuous pull), latch release 63 may be pushed by a section of trigger 50 towards the top part of handle 44 thus releasing the pre-coiled spring element 62. Once spring element 62 is released from the hold of latch release 63, it may expand and push compressor 61 towards the proximal end of delivery device 40. Following the movement of compressor 61 towards the proximal end of delivery device 40, pull-wire holder 60 along with pull-tab 51 are pushed in the same direction, thereby extending outside of delivery device 40. The protrusion of pull tab 51 out of delivery device 40 may indicate that capsule 18 is fully released from delivery device 40. Latch release 63 prevents inadvertent release of spring element 62 until trigger 50 is pulled all the way through.

Figure 4:
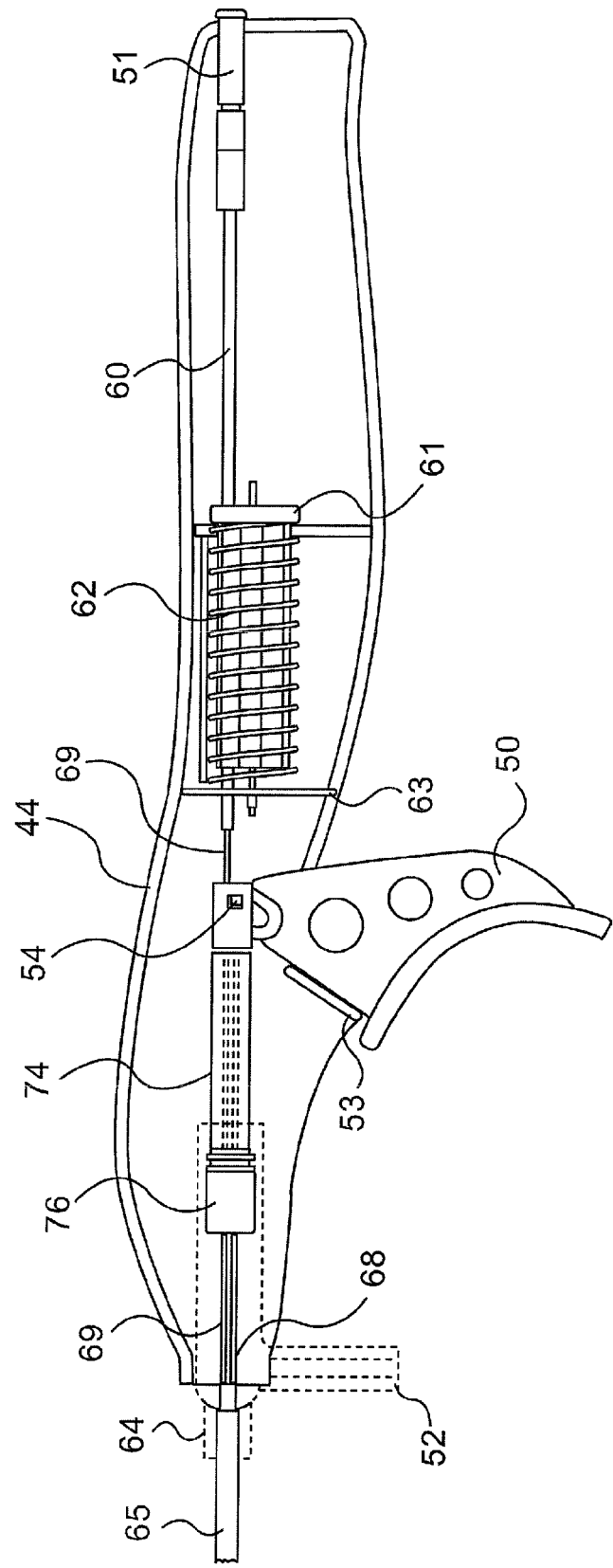
FIG. 4 is a cross-sectional side view of a handle portion of the delivery device according to an embodiment of the invention shown in FIG. 2.

Reference is made to FIG. 4, which is a cross-sectional view of a side of a handle 44 of exemplary delivery device 40. A user of delivery device 40 may interact with actuator 50 of handle 44 to anchor capsule 18 to the tissue location of interest and to release capsule 18 from delivery device 40. Initially, actuator 50 is held in place by safety lock 53, however, when safety lock 53 is removed, actuator (or trigger) 50 may be pulled back in the direction of the proximal end of delivery device 40, and may turn around its pivot 54. Spring element 62 may be coiled and may stay coiled as long as actuator 50 is not entirely pulled back. At this initial position, the T-tube vacuum seal 76 may be located at a distance from vacuum inlet 52 thus allowing negative pressure to maintain through vacuum inlet 52 and further through delivery device 40 as soon as vacuum source 30 is attached to vacuum inlet 52. Vacuum inlet 52 and tube 65 create a vacuum chamber within delivery device 40. In particular, the vacuum chamber extends from vacuum inlet 52 through tube 65 and into a void 84 of capsule 18.

After suction is applied to draw tissue into void 84 of capsule 18, actuator 50 is pulled back pushing push-wire 68 forward (towards the distal end of delivery device 40). The advancement of push-wire 68 causes an anchor element 85 to anchor capsule 18 to the tissue within void 84. In this position, the T-tube vacuum seal 76 is still in its initial position at a distance from vacuum inlet 52 and thus the vacuum chamber is still intact.

Pulling trigger 50 may cause T-tube stem 74 to be pushed forward (toward the distal end of delivery device 40) thus pushing T-tube vacuum seal 76 forward to its new position, which is over the opening of vacuum inlet 52. T-tube seal 76 may then seal vacuum inlet 52, thereby stopping the suction force through delivery device 40. When this occurs, the vacuum chamber within delivery device 40 is vented, e.g., atmospheric pressure enters the delivery device 40, and thus release of the capsule may be achieved more easily. In other embodiments, the suction force caused by the attached vacuum source 30 may be manually controlled by the user of delivery device 40.

When continuing to pull trigger 50 all the way through until its motion is stopped by contact with handle 44, latch release 63 may be pushed toward the upper side of handle 44. Spring element 62 is attached to compressor 61 and may be kept in a coiled state as long as latch release 63 holds compressor 61 preventing it from moving in any direction. Since latch release 63 is pushed up during activation of trigger 50, compressor 61 is free to move and spring element 62 attached to compressor 61 is free to expand backwards, towards the proximal end of delivery device 40. When spring element 62 expands and moves backwards, so does compressor 61. Compressor 61 may include pull-wire 69 passing through it. Pull-wire 69 passes through compressor 61 into pull-wire holder 60, while its other end may pass along tube 65 (which connects between T-tube 64 and capsule cradle 66), reach the capsule cradle 66 and pass through an opening in protrusion 81 of capsule 18. Pull-tab 51 is attached to pull-wire 69 as a continuation of pull-holder 60. Once compressor 61 is pushed back (along with spring element 62), pull-wire 69 which passes along pull-wire holder 60 may be pulled back thus pulling pull tab 51 outside of handle 44. Pull-tab 51 extending out from handle 44 may indicate safe release of capsule 18 from delivery device 40. When pull-wire 69 is pulled towards the proximal end of delivery device 40, it is in fact pulled outside of the opening in protrusion 81 of capsule 18 (FIG. 7C), such that capsule 18 may no longer be attached to delivery device 40.

Figure 5A:
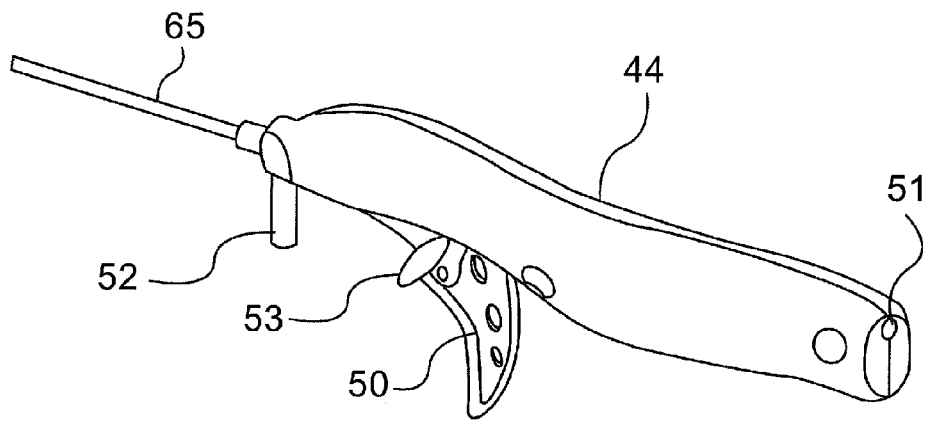
FIGS. 5A and 5B are perspective diagrams of a handle portion of the delivery device according to an embodiment of the invention shown in FIG. 2, illustrating position of components of the handle before and after actuation.
Figure 5B:
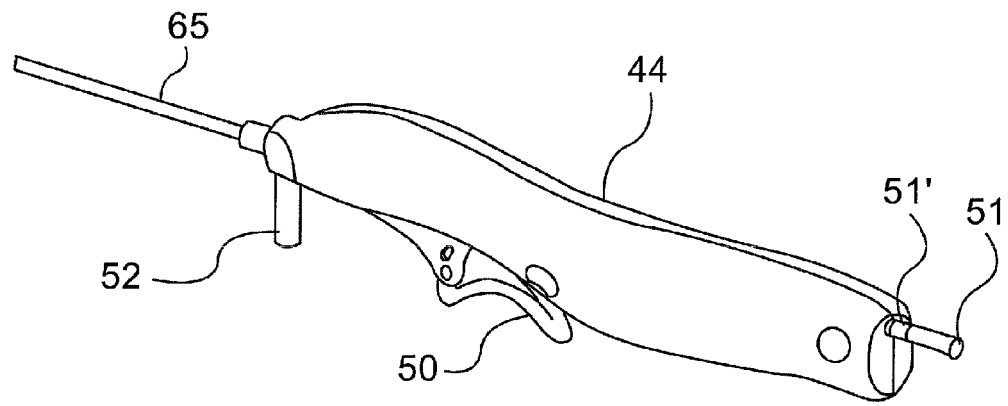

Reference is made to FIGS. 5A and 5B which are perspective diagrams of a handle portion of the delivery device of FIG. 2 illustrating position of components of the handle before and after actuation. FIG. 5A illustrates the handle 44 of delivery device 40 before actuation. Safety lock 53 is inserted through trigger 50 to prevent inadvertent event of actuating trigger 50 before it is intended to, e.g. during packaging, shipping, unpacking, and when vacuum is applied through vacuum inlet 52. Before actuation pull tab 51 is located within handle 44.

FIG. 5B illustrates components of handle 44 after actuation of trigger 50. Safety lock 53 is no longer attached to trigger 50, thus enabling trigger 50 to be pulled all the way through until it contacts handle 44, which causes its pulling motion to stop. Pull tab 51 may then extend outside of handle 44 thus indicating safe release of capsule 18 from delivery device 40. According to some embodiments, pull tab 51 may have a mark 51', which may be marked with a noticeable color at a desired location along pull tab 51. The location of mark 51' along pull-tab 51 may be chosen according to the minimum distance that pull-wire 69 is pulled at, such that pull-wire 69 would no longer be passed through capsule 18, i.e. that pull-wire 69 would no longer be connecting between capsule 18 and delivery device 40. Other locations of mark 51' may be used.

Mark 51' may be marked around the circumference of pull-tab 51. When the section of pull-tab 51 that includes mark 51' is pushed outside of handle 44, it may be an indication of full and safe release of capsule 18 from delivery device 40. If the pull-tab 51 extends from handle 44 but its section marked with mark 51' is still inside handle 44, it may indicate that pull-wire 69, which passes through tube 65 that connects between handle 44 and capsule 18, was not fully retracted outside of protrusion 81 of capsule 18 and outside of its corresponding dent 83 in delivery device 40 (FIG. 7C), i.e. capsule 18 is still attached to delivery device 40. In such an event, the operator of delivery device 40 may manually pull pull-tab 51 outside of handle 44 until mark 51' is noticed. That is, the operator may manually pull pull-wire 69 outside of protrusion 81 of capsule 18, since pull-wire 69 is an extension of pull-tab 51, thus manually releasing capsule 18 from delivery device 40. According to some embodiments, the operator may manually pull pull-tab 51 outside of handle 44 only once trigger 50 is pulled all the way through.

According to some embodiments, mark 51' may not be marked in a noticeable color, but rather mark 51' may be noticeable through other ways, e.g. by having a thinner diameter than that of the rest of pull-tab 51, or by having a different shape compared to the shape of the rest of pull-tab 51, etc.

Figure 6A:
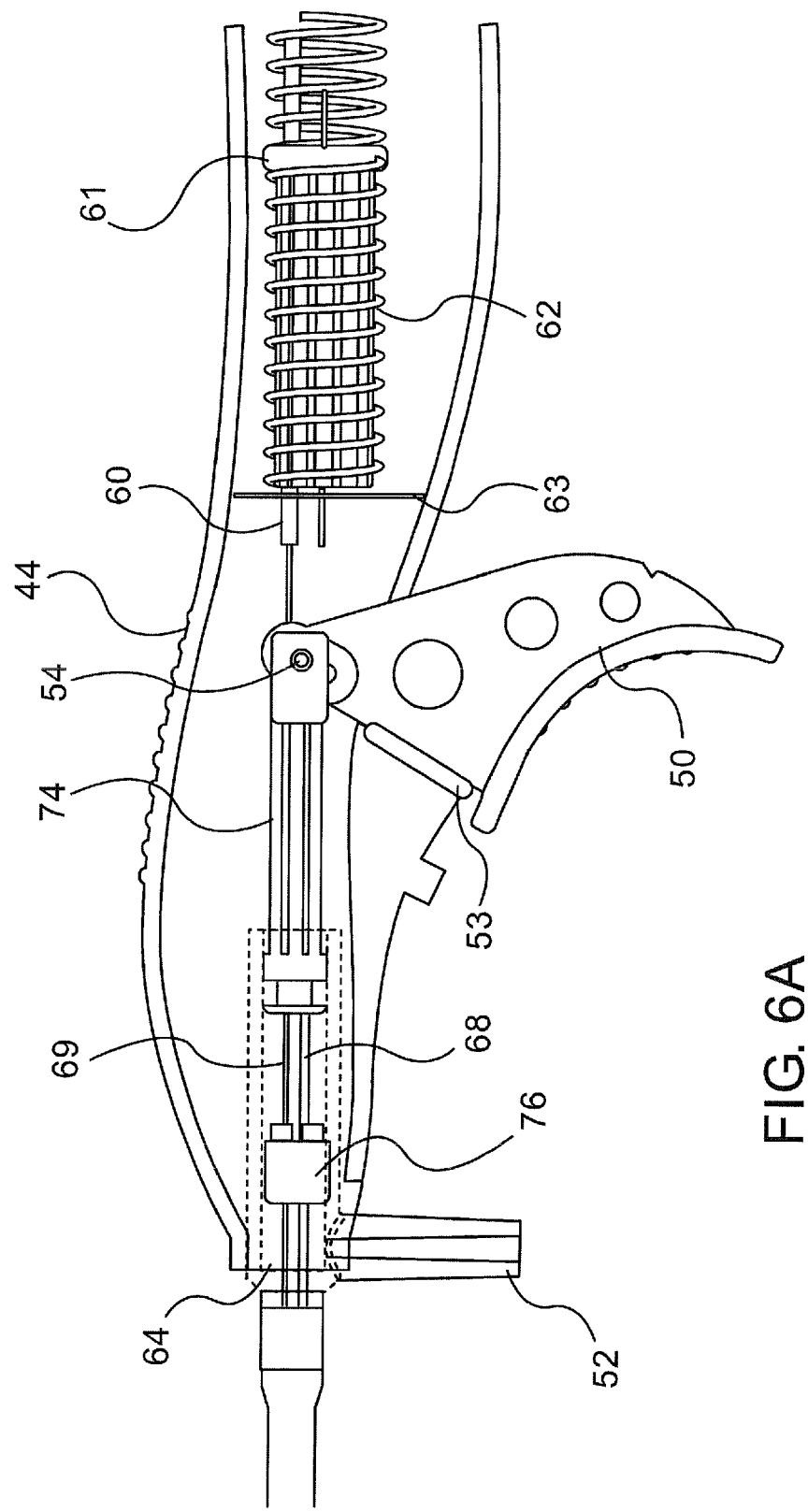
FIGS. 6A, 6B, and 6C are schematic diagrams illustrating exemplary operation of a handle portion of an exemplary delivery device according to an embodiment of the invention during various stages of delivery of a capsule.
Figure 6B:
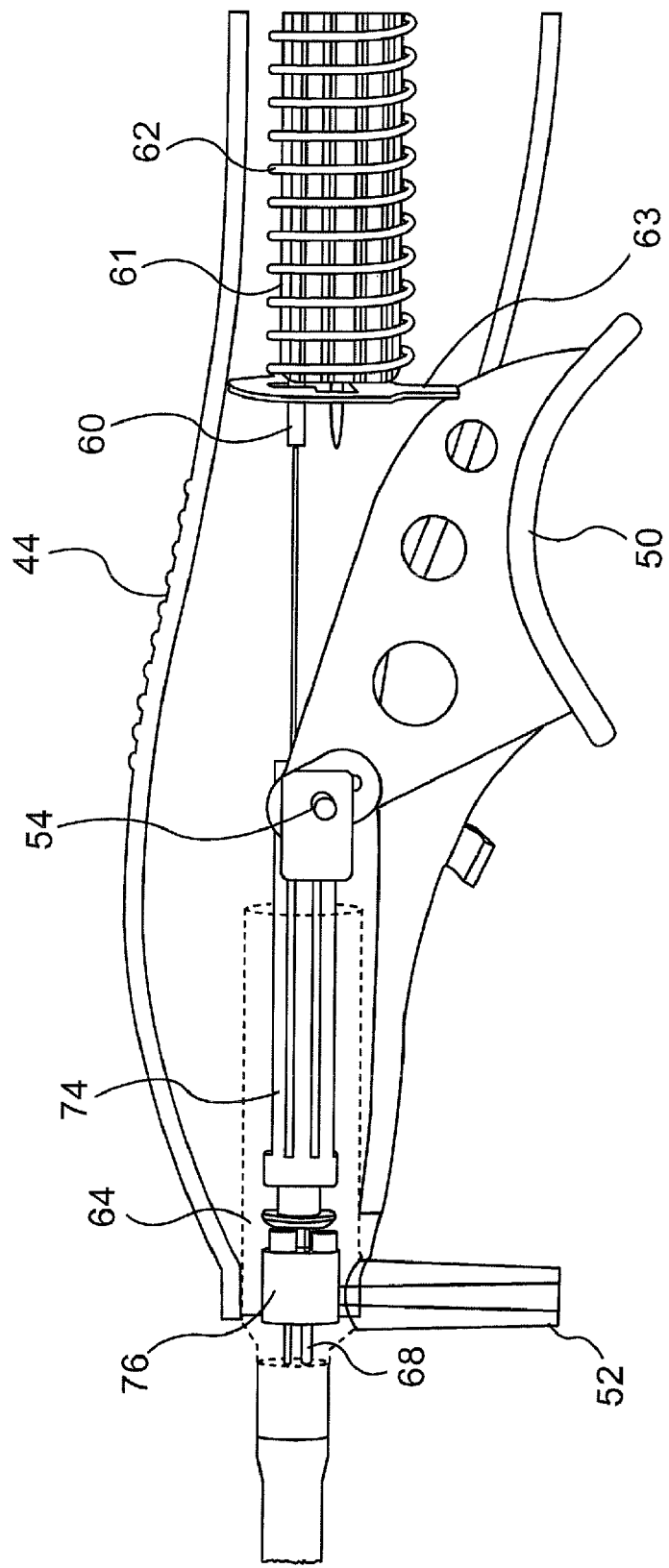
Figure 6C:
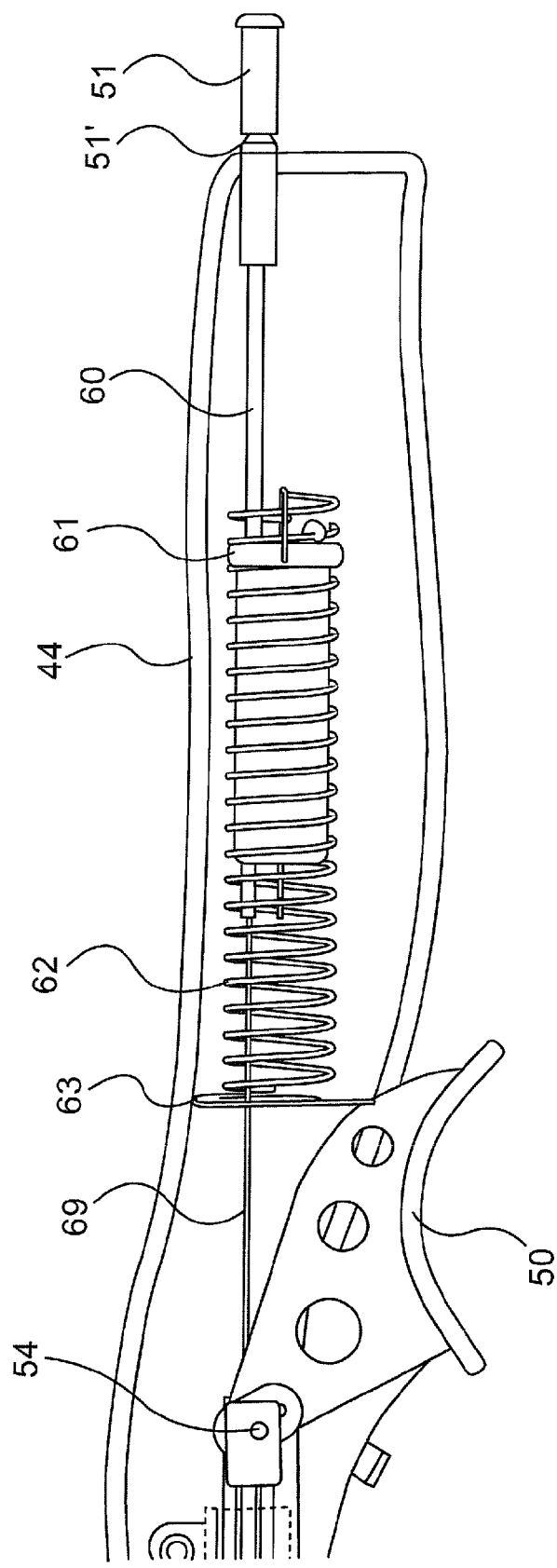

Reference is now made to FIGS. 6A, 6B, and 6C which are schematic diagrams illustrating exemplary operation of a handle portion of an exemplary delivery device according to embodiments of the present invention during various stages of delivery of a monitoring capsule. FIG. 6A illustrates a cross-section of delivery device 40 prior to actuation of trigger 50. Safety lock 53, which is inserted between handle 44 and trigger 50, prevents inadvertent actuation of trigger 50. As illustrated in FIG. 6A, T-tube vacuum seal 76, which is positioned within T-tube 64, is located at a distance from the opening of vacuum inlet 52, so as to allow suction to be applied through delivery device 40. Prior to actuation, latch release 63 holds spring element 62 along with compressor 61 in place, preventing spring element 62 from expanding backwards, towards the proximal end of delivery device 40.

FIG. 6B illustrates a cross-section of the distal end of delivery device 40, after actuation. When trigger 50 is pulled, it turns around its pivot 54, and pushes T-tube stem 74 forward, e.g., towards the distal end of delivery device 40. T-tube stem 74 moving forward causes push wire 68 to move forward thus causing an anchor element 85 to anchor capsule 18 to the tissue within void 84 (FIG. 7C). Furthermore, following the forward motion of T-tube stem 74 is the displacement of T-tube vacuum seal 76 towards vacuum inlet 52 until T-tube vacuum seal 76 covers the opening of vacuum inlet 52 thus preventing further suction, and allowing ventilation of delivery device 40. Sealing vacuum inlet 52 is the first step in releasing capsule 18 from delivery device 40.

FIG. 6C illustrates a cross-section of the proximal end of delivery device 40, after actuation. The second step in releasing the capsule 18 from delivery device 40 is pulling pull-wire 69 towards the proximal end of delivery device 40, thus retracting it from protrusion 81 of capsule 18 and its corresponding dent 83 in delivery device 40 (FIG. 7C). When trigger 50 is pulled all the way through it pushes latch release 63 up towards the upper part of handle 44. When latch release 63 is pushed up, spring element 62 may be free to expand towards the proximal end of delivery device 40, thus pushing compressor 61 which is attached to spring element 62. Since pull-tab 51 is attached to compressor 61, when spring element 62 and compressor 61 are pushed towards the proximal end of delivery device 40, pull-tab 51 may also be pushed, thus causing it to extend outside of delivery device 40. Pull-tab 51 extending outside of handle 44 may indicate on safe release of capsule 18 from delivery device 40. Pull-tab 51 is an extension of pull-wire holder 60, through which pull-wire 69 passes. Therefore, pull-tab 51 extending outside of handle 44 may indicate on full retraction of pull-wire 69 outside of capsule 18, thus indicating safe release of capsule 18 from delivery device 40.

Reference is now made to FIGS. 7A-7D which are schematic diagrams illustrating exemplary operation of a distal end of the delivery device according to embodiments of the invention during various stages of delivery of a capsule. FIG. 7A illustrates a side cross-section view of the distal end of the delivery device 40 occupying the capsule 18. As illustrated in FIG. 7A, the initial configuration of the distal end of delivery device 40 is such that the anchor element 85 is in an initial position within capsule 18. The initial position of anchor element 85 is such that it is located substantially outside of void 84 of capsule 18. The initial configuration of the distal end of delivery device 40 is the configuration in which the delivery device would be upon initiation of the capsule delivery procedure. The configuration illustrated in FIG. 7A corresponds with the configuration of the handle portion described above with reference to FIG. 6A. In particular, actuator 50 is prevented from initially moving towards the proximal end of delivery device 40. Since no movement of actuator 50 is permitted by safety latch 53, push-wire 68 cannot activate the release mechanism to inadvertently release capsule 18 from delivery device 40 before the capsule 18 is anchored to the tissue site, i.e. before anchor element 85 is in its final position.

In FIG. 7A, cradle 66 is a continuous part of tube 65, which holds capsule 18 attached to delivery device 40 while inserted into the esophagus. Cradle 66 has a dent 83 into which protrusion 81 of capsule 18 is inserted. Pull-wire 69 is threaded through parallel openings in protrusion 81 and dent 83 so as to attach capsule 18 to delivery device 40 before releasing the capsule 18 from the delivery device 40.

In some embodiments, there may be a seal 67 positioned between the capsule 18 and delivery device 40. Seal 67 may have an opening substantially in the middle, to allow application of vacuum through, and from delivery device 40 into capsule void 84, while ensuring no leak of vacuum to other areas. Seal 67 may ensure suction from vacuum inlet 52 is applied to capsule void 84 without leaking to other areas, e.g., outside of capsule 18. Seal 67 covers the entire interface between delivery device 40 and capsule 18 leaving only the opening in substantially the middle of it, through which vacuum may be applied. Typically, capsule 18 and delivery device 40 may not be tightly attached to one another due to the different materials they are made of, and thus due to their different surfaces. Therefore, there may be a need for an intermediator positioned in between the capsule 18 and delivery device 40, which may ensure the two are held tightly together and thus ensure vacuum is delivered into void 84 without any leaks. Seal 67 may seal the interface between delivery device 40 and capsule 18 (excluding its opening in the middle), so that a sufficient vacuum level is applied into void 84 and tissue may be properly sucked into void 84. Seal 67 may be made of foam like material; however, other materials may be used.

According to some embodiments, capsule 18 may comprise an antenna through which pH data acquired by the capsule 18 may be transferred to an external receiver 20 (FIG. 1). In some embodiments, the electrical components of capsule 18 may be powered by an internal power source 82, e.g. silver oxide batteries. Capsule 18 may further comprise a void 84 into which esophageal tissue may be sucked into, once vacuum source 30 (FIG. 1) is attached to the delivery device 40. According to some embodiments, delivery device 40 may comprise an anchor element 85, e.g. a pin, that may be pushed by push-wire 68 (during operation of actuator 50 (FIG. 2)) through void 84, in order to anchor capsule 18 to the esophageal tissue, as will be shown later.

Although a pin 85 is described for purposes of illustration, other types of anchoring elements may be used. U.S. Pat. Nos. 6,285,897 and 6,689,056 to Kilcoyne et al. provide examples of a variety of anchoring elements for attaching monitoring devices to the lining of the esophagus, e.g. adhesive substances, clips, staples, tacks, hooks, and barbs. Another example for an anchoring element as described in FIG. 5 of U.S. Pat. No. 6,285,897 is an elastic band, which may be placed around a protuberance in the wall of the esophagus 30. The anchoring elements described in the Kilcoyne et al. patents may be suitable for attachment of capsule 18.

FIG. 7B illustrates a bottom cross-section view of the distal end of delivery device 40 occupying capsule 18. In FIG. 7B, capsule 18 is still attached to delivery device 40, i.e. the figure illustrates the capsule prior to anchoring it to the esophageal tissue.

FIG. 7C illustrates a side cross-section view of the distal end of the delivery device occupying the capsule, after anchoring the capsule to the esophageal tissue. Upon identifying the appropriate location for placement of capsule 18, vacuum inlet 52 receives sufficient suction pressure from vacuum source 30 (FIG. 1) to draw a portion of esophageal tissue into a void 84 of capsule 18. Actuator 50 is pulled in a pivot motion to cause delivery device 40 to anchor capsule 18 to the esophageal tissue. More specifically, the pivot movement of actuator 50 causes push-wire 68 to push anchor element 85 through the tissue within void 84 to anchor capsule 18 to the wall of esophagus 14 (FIG. 1). Anchor element 85 being pushed through the tissue that is sucked into void 84 is the final position of anchor element 85. The configuration illustrated in FIG. 7C corresponds with the configuration of the handle portion described above with reference to FIG. 6B.

In FIG. 7C, anchor element 85 is inserted through void 84, i.e. pin 85 is inserted through the esophageal tissue that was previously sucked into void 84. In some embodiments, once the operator of delivery device 40 finds the proper location along the esophagus where the capsule 18 should be attached, the operator turns on the vacuum source 30 (FIG. 1) thereby causing suction of esophageal tissue into void 84 of the capsule 18. After the tissue is sucked into void 84, the operator of delivery device 40 pulls trigger 50 which causes push-wire 68 to move towards the distal end of delivery device 40, and thus to push anchor element 85 through the sucked tissue.

FIG. 7D illustrates a side-view of the distal end of the delivery device following release of the capsule from the delivery device. After capsule 18 is anchored to the wall of esophagus 14, actuator 50 is further moved in a pivot motion causing pull-wire 69 to retract toward handle 44 of delivery device 40. The configuration illustrated in FIG. 7D corresponds with the configuration of the handle portion described above with reference to FIG. 6C.

In FIG. 7D, anchor element 85 is passed through the esophageal tissue sucked into void 84 in capsule 18. Thus following release of capsule 18 from delivery device 40, anchor element 85 remains with capsule 18 and is no longer connected to delivery device 40. According to some embodiments, during the operation of actuator 50, push-wire 68 is passed through seal 67 and extends through delivery device 40 in order to push anchor element 85 into the tissue sucked into void 84 (FIG. 7C). In FIG. 7D push-wire 68 extends out of delivery device 40 illustrating that it pushed pin 85 through the sucked esophageal tissue in order to anchor capsule 18 to the esophagus wall. During the operation of actuator 50 and after pin 85 is passed through the esophageal tissue, vacuum inlet 52 (FIG. 6B) is closed in order to cease suction through delivery device 40 and thus to ease release of capsule 18 from delivery device 40. Furthermore, during operation of trigger 50, pull-wire 69 (FIG. 7C) is pulled towards the proximal end of delivery device 40, thereby freeing the opening in protrusion 81 of capsule 18. Retracting pull-wire 69 away from protrusion 81 (and thus away from dent 83) corresponds to releasing capsule 18 from delivery device 40, as shown in FIG. 7D.

Figure 8:
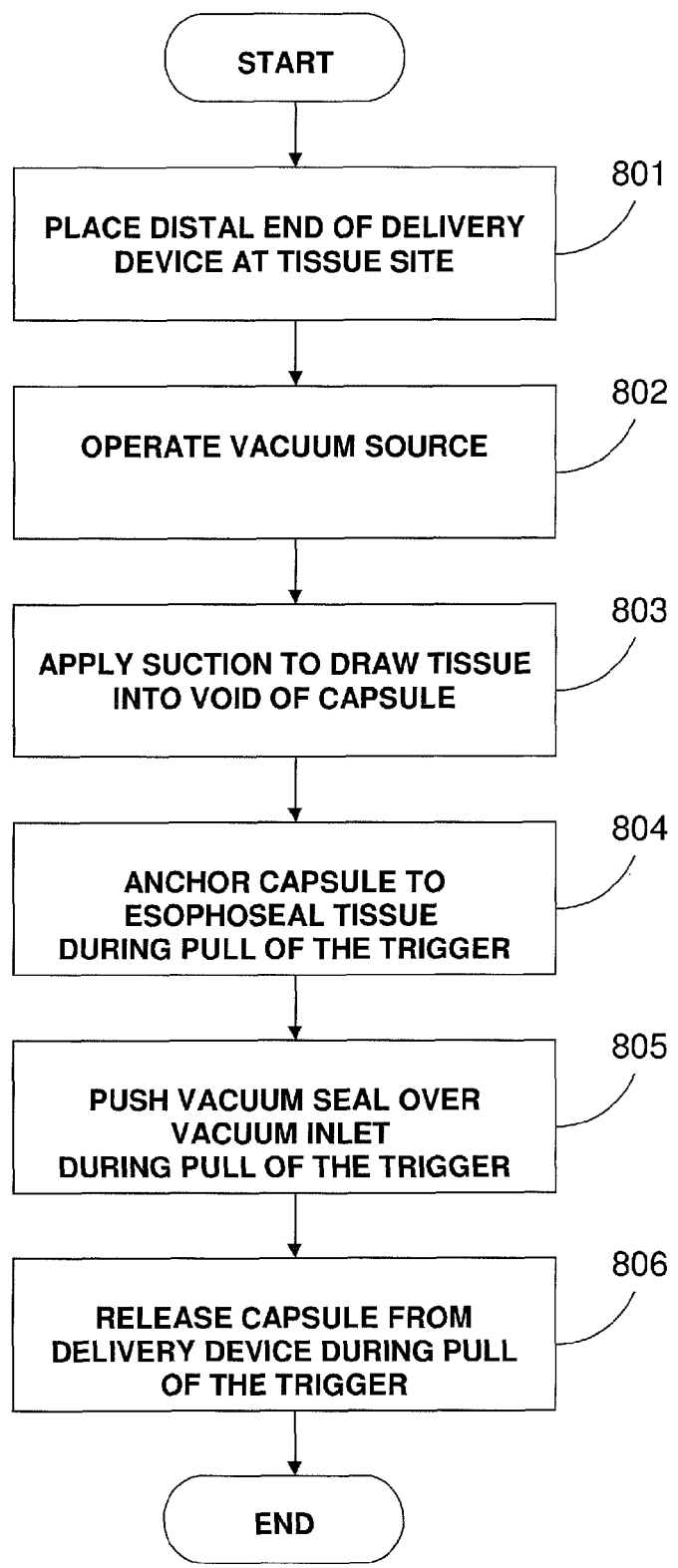
FIG. 8 is a flow diagram illustrating exemplary operation of a delivery device according to an embodiment of the invention for placing a capsule at a location within the body lumen of a patient.

Reference is made to FIG. 8 which is a flow diagram illustrating exemplary operation of a delivery device placing a capsule at a location within a patient. In some embodiments, FIG. 8 is a flow diagram illustrating operation of delivery device 40 placing capsule 18 to an esophagus of a patient. Initially, the operator of delivery device 40 places the distal end of delivery device 40 at tissue at a site of interest (801). In particular, the distal end of delivery device 40 enters esophagus 14, via either the nasal or oral cavity, and extends through esophagus 14 to the LES.

Upon identifying the appropriate location for anchoring of capsule 18, the operator of delivery device 40 operates vacuum source 30 (802). Delivery device 40 receives suction pressure from vacuum source 30 to draw esophageal tissue into a void of capsule 18 (803). The operator of delivery device 40 anchors capsule 18 to the wall of esophagus 14 during a pull motion of an actuator (804). For example, delivery device 40 may advance push-wire 68 to drive a locking pin 85 through the esophageal tissue in the void 84 of capsule 18 to anchor the capsule 18 when trigger 50 is pulled and turned around its pivot.

After anchoring capsule 18 to esophagus 14, delivery device 40 pushes T-tube vacuum seal 76 over vacuum inlet 52 during the same pull motion of the trigger 50 (805). Further during the same continuous pull motion of trigger 50, the operator of delivery device 40 releases capsule 18 from delivery device 40, thereby leaving capsule 18 anchored to esophagus 14 (806). For example, movement of trigger 50 may cause pull-wire 69 to retract from capsule's protrusion 81, thus releasing capsule 18 from the delivery device 40.

While anchored on the wall of esophagus 14, one or more sensors within capsule 18 may obtain measurements, such as acidity measurements, within esophagus 14, and capsule 18 relays the measurements to receiver 20 via wireless communication (FIG. 1). In some embodiments, capsule 18 may transmit the measurements to receiver 20 and/or to an external or implanted therapy device, such as an electrical neurostimulator or a drug delivery device. A neurostimulator, drug delivery device, or other therapeutic device may be responsive to measurements obtained by capsule 18 to delivery therapy based on the measurements. Alternatively, a neurostimulator, drug delivery device, or other therapeutic device may be responsive to commands transmitted by receiver 20 to the device, in which case receiver 20 generates the commands based on the measurements obtained by capsule 18.

Although the embodiments described in this disclosure relate to placement of a capsule for sensing acidity of esophagus of the patient, the techniques of the disclosure may be applied for delivery of other types of sensors to different body lumens, tissue locations or organs within a patient. Moreover, the techniques of this disclosure may be used to place other therapeutic devices, such as neurostimulators, drug delivery devices, drug release devices, or other devices to locations within a patient. The techniques and system of this disclosure may be used to place in the stomach or other location in the gastrointestinal tract an intra-luminal device for gastrointestinal electrical stimulation such as one of such devices described in U.S. patent application Ser. No. 10/801,230, published as Publication No. 2005/0209653 to Herbert, et al., the entire content of which is incorporated herein by reference. For example, such a system may be used to sense physiological conditions within different body lumens, such as the esophagus, stomach, intestines, urethra, bladder, or colon. In urinary tract applications, for example, the system may be adapted for urodynamic testing, urinalysis, or other diagnostic evaluations pertinent to the urinary tract, e.g., as described in U.S. Published Patent Application No. 2005/0245840 to Christopherson et al., the entire content of which is incorporated herein by reference. Moreover, the techniques are not limited to application for monitoring associated with any particular disorder, condition or affliction. As further examples, a monitoring device in accordance with the techniques of this disclosure can be used to monitor other types of physiological conditions, such as conditions indicative of pregnancy, ovulation, or the condition of a fetus.

The preceding specific embodiments are illustrative of the practice of the techniques of this disclosure. It is to be understood, therefore, that other expedients known to those skilled in the art or disclosed herein may be employed without departing from the scope of the following claims.

What is claimed is:

1. A device comprising:
   an elongated probe configured to carry at a distal end thereof an implantable capsule for deployment within a patient;
   a vacuum inlet configured to apply suction through the device and to draw tissue into a void comprised in said capsule;
   an anchor element configured to anchor the capsule to the drawn tissue within the patient;
   a release mechanism configured to release the capsule from the probe, said release mechanism comprising a vacuum seal, a spring element, and a pull-wire for coupling the capsule to the device; and
   an actuator located at the proximal end of the elongated probe configured to push the anchor element to anchor the capsule to the tissue, and to push the vacuum seal to cover an opening of said vacuum inlet, and to release said spring element to expand towards the proximal end of the device, thereby retracting the pull-wire to release the capsule from the probe, said actuator to cause said anchoring, said covering and said releasing by a single motion of the actuator.

2. The device of claim 1, wherein the single motion comprises a pulling motion.

3. The device of claim 1, wherein the actuator comprises a movable trigger.

4. The device of claim 1, wherein said vacuum inlet is adapted to be coupled to a vacuum source, to provide suction through the vacuum inlet.

5. The device of claim 1, wherein the anchor element comprises a locking pin, and further wherein the actuator engages with the locking pin to advance the locking pin through the tissue during the single motion.

6. The device of claim 5, wherein the device comprises a push-wire, wherein the actuator engages with the push-wire to advance the locking pin through the tissue during the single motion of the actuator.

7. The device of claim 1, further comprising a locking mechanism that prevents the trigger to move before pulled by the operator.

8. A method comprising:
   delivering an implantable capsule to tissue within a patient using a delivery device, the delivery device comprising:
   an elongated probe configured to carry at a distal end thereof the implantable capsule for deployment within a patient;
   a vacuum inlet configured to apply suction through the device and to draw tissue into a void comprised in said capsule;
   an anchor element configured to anchor the capsule to the drawn tissue within the patient;
   a release mechanism configured to release the capsule from the probe, said release mechanism comprising a vacuum seal, a spring element, and a pull-wire for coupling the capsule to the device; and
   an actuator located at the proximal end of the elongated probe configured to push the anchor element to anchor the capsule to the tissue, and to push the vacuum seal to cover an opening of said vacuum inlet, and to release said spring element to expand towards the proximal end of the device, thereby retracting the pull-wire to release the capsule from the probe, said actuator to cause said anchoring, said covering and said releasing by a single motion of the actuator;
   anchoring the implantable capsule to the tissue; and
   releasing the capsule from the delivery device, wherein anchoring the capsule and releasing the capsule are done during a single motion of the actuator of the device.

9. The method of claim 8, wherein anchoring the capsule to the tissue comprises advancing a locking pin through the tissue during the single motion of the actuator.

10. The method of claim 8, further comprising coupling the capsule to a distal end of the device using the pull-wire, wherein releasing the capsule from the device comprises retracting the pull-wire to release the capsule.

11. The method of claim 8, wherein the capsule includes a sensor and further comprising: measuring one or more parameters of the patient via the sensor of the capsule; and transmitting the measured parameters from the capsule to a receiver.

12. A device comprising:
   an elongated probe for carrying an implantable capsule for deployment within a patient;
   a vacuum inlet for as applying suction through the device and for drawing tissue into a void in said capsule;
   an anchor element for anchoring the capsule to the tissue within the patient;
   a release mechanism for releasing the capsule from the probe; and
   an actuator for activating by a single motion of the actuator the anchor element to anchor the capsule to the tissue and the release mechanism to cover the vacuum inlet and to release the capsule from the probe.

13. The device of claim 12, further comprising a coupling mechanism for coupling the capsule to the carrying probe, wherein the release mechanism causes the coupling mechanism to release the capsule during the single motion of the actuator.

14. The device of claim 12, further comprising a vacuum seal, wherein said actuator is configured to push the vacuum seal over the vacuum inlet during the single motion of the actuator such that suction is ceased.

15. The device of claim 12, further comprising a capsule coupling mechanism configured to couple the capsule to a distal end of the probe, wherein the release mechanism causes the capsule coupling mechanism to release the capsule during the single motion of the actuator.

16. The device of claim 15, wherein the capsule coupling mechanism includes at least one pull-wire configured to couple to the capsule, and further wherein the release mechanism causes the pull-wire to retract and thereby to release the capsule during the single motion of the actuator.

17. The device of claim 12, wherein the anchor element comprises a locking pin, and further wherein the actuator engages with the locking pin to advance the locking pin through the tissue during the single motion.

18. The device of claim 17, comprising a push-wire, wherein the actuator engages with the push-wire to advance the locking pin through the tissue during the single motion of the actuator.

19. A system comprising:
a delivery apparatus comprising:
an elongated probe configured to carry at a distal end thereof an implantable capsule for deployment within a patient;
a vacuum inlet configured to apply suction through the device and to draw tissue into a void comprised in said capsule;
an anchor element configured to anchor the capsule to the drawn tissue within the patient;
a release mechanism configured to release the capsule from the probe, said release mechanism comprising a vacuum seal, a spring element, and a pull-wire for coupling the capsule to the device; and
an actuator located at the proximal end of the elongated probe configured to control delivery of the capsule; and
wherein the actuator is configured to activate the anchor element to thereby push the anchor element to anchor the capsule to the tissue, and to activate the release mechanism to thereby push the vacuum seal to cover an opening of said vacuum inlet, and to release said spring element to expand towards the proximal end of the device, thereby retracting the pull-wire to release the capsule from the probe, said actuator to activate the anchor element and the release mechanism by a single motion of the actuator.

* * * * *